United States Patent [19]

Hortmann et al.

[11] Patent Number: 4,696,287

[45] Date of Patent: Sep. 29, 1987

[54] TRANSMISSION SYSTEM FOR IMPLANTED HEARING AIDS

[75] Inventors: Guenther Hortmann, Neckartenzlingen; Klaus Kunick; Hans Fenner, both of Stuttgart, all of Fed. Rep. of Germany

[73] Assignee: HORTMANN GmbH, Neckartenzlingen, Fed. Rep. of Germany

[21] Appl. No.: 833,989

[22] Filed: Feb. 26, 1986

[30] Foreign Application Priority Data

Feb. 26, 1985 [DE] Fed. Rep. of Germany ....... 3506721

[51] Int. Cl.$^4$ .............................................. A61N 1/30
[52] U.S. Cl. .................................... 128/1 R; 128/421; 128/419 R; 381/68
[58] Field of Search ............... 128/1 R, 784, 785, 789, 128/419 R, 420, 421; 179/107 R, 107 BC, 107 E, 107 H; 381/68, 68.5

[56] References Cited

U.S. PATENT DOCUMENTS 4,352,960 10/1982 Dormer et al. .............. 179/107 BC
4,419,995 12/1983 Hochmair et al. .......... 179/107 R X
4,532,930 8/1985 Crosby et al. ................... 128/421 X

OTHER PUBLICATIONS

Gheevala et al, "CMOS Implantable . . . Stimulator for the Dent", IEEE Jrnl. Sol. St. Linc., vol. SC10, No.6, 12/75.

Primary Examiner—Edward M. Coven
Attorney, Agent, or Firm—Michael J. Striker

[57] ABSTRACT

An implanted hearing aid for deaf patient having an intact auditory nerve includes an implanted receiver unit provided with a receiver coil surrounding patient's auditory channel. An external transmitter unit is electrically connected to a separate transmitter coil embedded in a fitting piece insertable into the auditory channel in the range of the receiving coil so as to establish an optimum inductive coupling. A microphone is supported on an ear yoke and connected both to the transmitter and the receiver units. The receiver unit is electrically connected to an excitation electrode mounted on cochlea in patient's ear.

6 Claims, 2 Drawing Figures

TRANSMISSION SYSTEM FOR IMPLANTED HEARING AIDS

BACKGROUND OF THE INVENTION

The present invention relates to a transmission system for implanted hearing aids of the type having at least one implanted excitation electrode, an acoustic convertor with a corresponding circuit, a high frequency transmitter cooperating with the convertor and transmitting by means of a transmitter coil, an implanted receiver unit including at least one receiver coil and being electrically connected to the excitation electrode.

From prior art it is known how to excite electrically the inner ear of totally deaf patients whose auditory nerve is still intact. For this purpose, a mono- or multi-electrode is inserted in the cochlea of the patient, the electrode being provided with distributed contact members which are excitable via a receiver unit by high frequency signals generated by an external transmitter unit, thus producing an acoustic sensation in the auditory nerve of the patient. The acoustic convertor converts the received sound waves into electrical signals which are processed in a suitable electrical evaluation circuit whose construction is well known in the art and therefore it will not be discussed in connection with this invention. The evaluation circuit shapes the electric acoustical signals, decodes these signals and distributes them into a series of frequency channels selected such that the corresponding signals transferred by the implanted high frequency receiver excite the auditory nerve of the patient in the most natural way that is to simulate the natural sound conversion in the inner ear in the most accurate way.

When transmitting signals generated by an external high frequency transmitter and coupling these signals via a transmitter coil to a coil of the implanted high frequency receiver, there is a problem of an adjustment of the inductive coupling between the transmitter and receiver coils. It is desired to provide a coupling which minimizes the consumption of energy from the minute battery pertaining to the transmitter and receiver units. In prior art solutions in order to place the transmitter coil in close proximity to the receiver coil, the transmitter coil has been arranged on a crown yoke, on a head band, in a frame for glasses or in a separate ear yoke in such a manner as to contact the skin behind the auricle of the patient opposite the implanted receiver coil. The disadvantage of this prior art arrangement is the fact that an exact alignment of the transmitter coil with the receiver coil is obtained only accidentally and due to unavoidable shaking resulting from movements of the patient the aligned position in practice cannot be maintained for a prolongated period of time. Attempts have been made to create a centrally aligned coupling position of the transmitter and receiver coils by means of a magnetic holder for the receiver coil whereby an extremely strong permanent magnet made of lanthanide series substances is provided in the center of the implanted receiver coil and a magnetizable counter piece is arranged in the center of the external transmitter coil so that the latter is automatically centered and held in position by the strong magnetic forces. In this solution the transmitter coil contacts the skin of the patient under pressure thus rendering it susceptible to inflammation in the range of the implanted receiver coil where the patient had undergone a surgical operation.

In addition conventional arrangements of transmitter and receiver coils have cosmetic and psychological disadvantages because the transmitter and its holder is conspicuous and adds to the psychological discomfort of deaf persons during social communication.

SUMMARY OF THE INVENTION

It is therefore a general object of the present invention to overcome the disadvantages of prior art implanted hearing aids.

In particular, it is an object of this invention to provide an improved electromagnetic coupling between the transmitter and receiver coils whereby the nonimplanted transmitter coil is reliably held in a fixed position relative to the receiver coil.

Another object of this invention is to provide such an improved arrangement of the transmitter coil which does not require any additional holding magnets, does not irritate skin of the patient and is inconspicuous in appearance.

In keeping with these objects and with others which will become apparent hereafter, one feature of this invention resides in the provision of a fitting piece insertable into the external auditory channel of a patient's ear, the transmitter coil being embedded in the fitting piece, and the implanted receiver coil being in the form of a ring which surrounds the auditory channel in such a way that the embedded transmitter coil is concentric with the receiver coil. In one embodiment, the receiver coil can be spatially separated from the implanted receiver unit whereas in another embodiment the entire receiver unit together with the receiver coil may be designed as an annular body surrounding the auditory channel.

In the former case, only the separated receiver coil can be implanted around the auditory channel by the requisite surgical operation. The receiver coil can be in the form of several windings of a thin wire of medically safe silver or if desired, in the form of a thin insulating wire covered by a medical teflon; the receiver coil in this modification can be wound around the auditory channel of the patient in such a manner that the tubular channel is not severed and need not be sewed together after the operation. The used materials of the receiver coil guarantee an irritation-free implantation of the coil in the body tissues. Also the transmitter coil which can be arranged on a cylindrical core whose center axis extends substantially at right angles to the plane of the receiver coil is embedded in the fitting piece made of a material which is tolerated by patients skin, for example a silicon based substance. The exact position of the fitting piece in the patient's auditory channel can be determined individually depending on individual conditions of the patient that means the configuration of the fitting piece is adjusted individually. Preferably however the fitting piece has a standard shape and is connected via a longitudinally adjustable tension-proof and flexible insulating and protective pipe with a hook shaped ear yoke suspended on patient's ear. With advantage, the ear yoke supports also the acoustic convertor in the form of a directional microphone. The flexible insulating and protective pipe encloses all electrical conductors leading from the acoustic convertor to the separate transmitter unit and to the transmitter coil. The arrangement of the transmitter coil according to the invention guarantees that the transmitter coil is always situated exactly at the center of the receiver coil and consequently an optimum transmission factor will result. It has been proved that in comparison with conventional couplings between the transmitter and receiver coils, an improvement of the transmission factor up to 50% can be achieved. As a consequence, the requisite transmitter power can be substantially reduced and at a given capacity of the battery, the service life of the entire transmission system is considerably prolongated. Alternatively, the battery can be reduced in size and consequently the overall device becomes smaller and lighter.

The coupling arrangement between the transmitter and receiver coils in accordance with this invention contributes substantially to the hiding of the hearing aid and from the microphone supporting a yoke it cannot be recognized whether the hearing aid is designed for deaf persons of for persons who have minor hearing problems. In the embodiment in which the receiver coil is spaced apart from the receiver unit the latter can be implanted at an arabitrary location under skin, thus simplfying the surgical operation. An additional advantage of this invention is the fact that the thickness of patient's skin over the implanted receiver part and hairs in the range of the receiver unit can no longer impair the transmission quality. The receiver coil is situated practically in all cases at the same zone around the auditory duct. The auditory channel or duct is easily accessible for receiving the transmitter coil carrying fitting piece and insures a stable seat for the piece on patient's body. Consequently, vibrations resulting from movements of the patient for example during dancing have no interfering effect on the coupling between the transmitter and receiver coils.

Still another advantage resulting from the optimum coupling between the transmitter and receiver coils and from the reduced transmitting power is the fact that the radiation of the transmitter coil has only a negligible effect on the acoustic convertor and consequently the microphone similarly as in the hearing aids for hard of hearing persons, can be located directly over the ear. Hence, the patient still preserves the capability to find the direction of acoustical sources and by turning the head it can distinguish among several sources of sound.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENT

Figure 1:
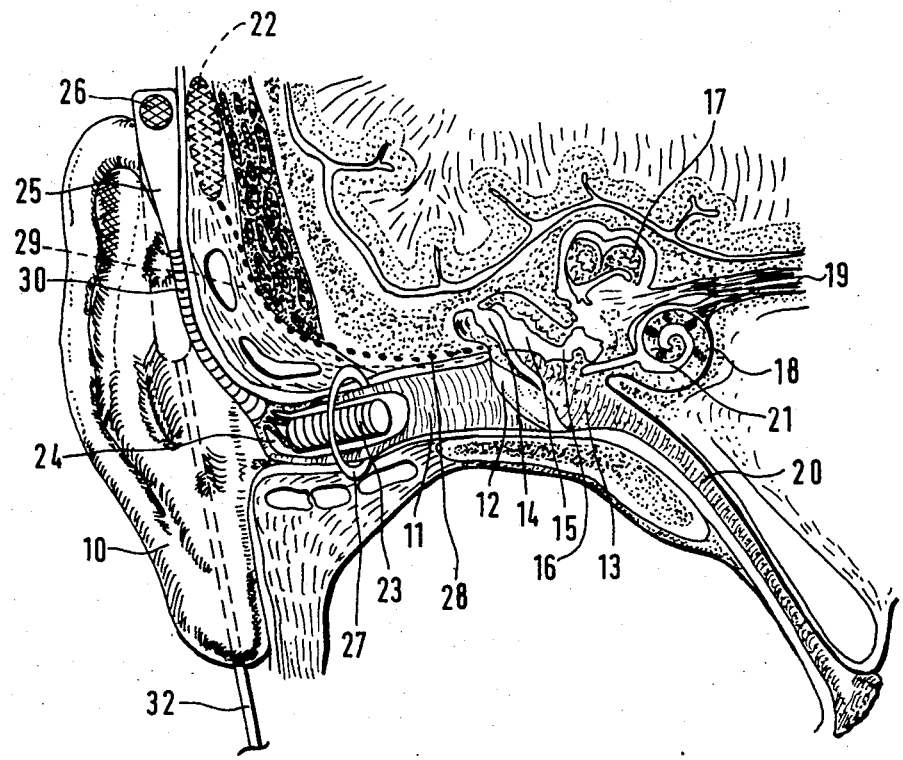
FIG. 1 is a sectional view of human ear with implanted hearing aid transmission system of this invention.

Referring to FIG. 1, the illustrated cross section of human ear shows auricle 10, auditory channel 11 terminating at tympanic membrane 12, the middle ear with tympanic cavity 13, auditory ossicles with hammer 14, anvil 15 and stirrup 16, the labyrinth 17, cochlea 18, the auditory nerve 19 leading to the cochlea and the eustachian tube 20.

The multi-frequency hearing aid system includes an excitation electrode plate 21 implanted in the cochlea, a receiver unit 22 implanted behind the auricle and a fitting piece 24 made of a silicon based material and being inserted into the auditory channel. The fitting piece encloses transmitter coil 23 wound on a cylindrical ferrite core. The hearing aid further includes an ear yoke 25 suspended on the top part of auricle and supporting an acoustic converter in the form of a directional microphone 26. A ring-shaped receiver coil 27 is implanted in patient's ear around the auditory channel 11.

Electrical conductors connecting the implanted receiver unit 22 with individual excitation electrodes supported on the electrode plate 21 and conductors leading to the receiver coil 27 are illustrated in FIG. 1 schematically by dashed lines 28 and 29.

The transmitter coil 23 embedded in the fitting piece 24 is connected to an external transmitter unit by electrical conductor lines through a flexible, tension proof insulating and protecting tube 30 connected at one end to the ear yoke 25 and to the fitting piece 24 at the other end. As mentioned before, the transmitter coil 23 is wound on a cylindrical ferrite core which in the inserted position of the fitting piece extends substantially perpendicularly to the plane of the implanted receiver coil 27 surrounding the auditory channel. The separate transmitter unit 31 (FIG. 2) of the transmission system of this invention is located together with a power supply battery in a housing normally carried on patient's body, suspended for example on a belt. The transmitter unit 31 includes an evaluation circuit for electrical signals delivered by microphone 26 and high frequency transmitters for individual frequencies. FIG. 1 illustrates also a connection cable 32 for connecting the transmitter coil and the microphone on the ear yoke 25 to transmitter unit 31.

Upon insertion of the fitting piece into patient's ear, the transmitter coil 23 is located exactly at the center of the ring-shaped receiver coil 27. The receiver coil can be formed of only three windings of a skin compatible insulated wire of medically safe pure silver.

Figure 2:
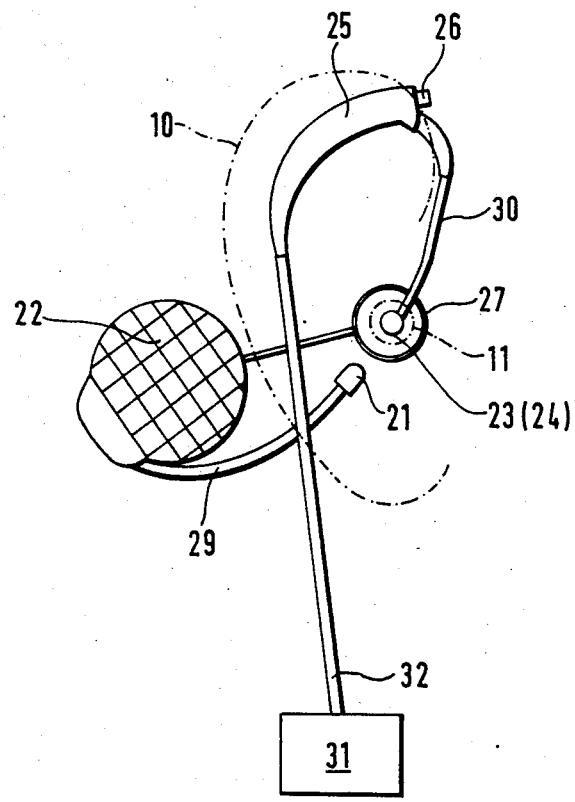
FIG. 2 is a schematic representation of the arrangement of components parts of the transmission system of this invention.

The schematic illustration of the layout of component parts of a multi-frequency transmission system of this invention is shown in FIG. 2. Auricle 10 and auditory channel 11 of a patient are indicated by dashed lines. The auricle supports the ear yoke 25 with microphone 26. FIG. 2 illustrates schematically in a front view the connection of fitting piece 24 and of the embodied transmitter coil 23 with the ear yoke by means of a flexible insulating and protecting tube 30 enclosing the corresponding connection wires. It will be also seen the concentric arrangement of the transmitter and receiver coils 23 and 27. In this embodiment, the receiver coil 27 is separated from the implanted receiver unit 22 and is connected thereto by an implanted conductor. Additional implanted conductors 28 and 29 connect the receiver unit 22 with nonillustrated excitation electrodes of the electrode plate 21 attached to the cochlea. The connection cable 32 connects the microphone 26 and the transmitter coil 23 with an external transmitter unit 31 containing also power supply battery.

While the invention has been illustrated and described as embodied in a specific example of a transmission system for an implanted hearing aid, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A transmission system for an implanted hearing aid, comprising at least one excitation electrode implanted in a patient's ear, an implanted receiver unit provided with a receiver coil, said receiver coil surrounding auditory channel of the ear; a transmitter unit provided with a separate transmitter coil, an acoustic converter coupled via said transmitter and receiver units to said excitation electrode, a fitting piece enclosing said transmitter coil, said fitting piece being inserted in said auditory channel at a position at which said transmitter coil is concentric with said receiver coil and a stable inductive coupling between said coils is established.

2. A transmission system as defined in claim 7, wherein said receiver coil has a ring-shaped configuration and consists of several windings of pure silver wound around the auditory channel and being connected to the implanted receiver unit.

3. A transmission system as defined in claim 2, wherein said receiver coil is separated from the implanted receiver unit.

4. A transmission system as defined in claim 2, wherein the entire receiver unit inclusive of the receiver coil has a ring-shaped configuration surrounding the patient's auditory channel.

5. A transmission system as defined in claim 4, wherein the transmitter coil is wound on a cylindrical ferrite core whose longitudinal axis upon insertion of the fitting piece into the auditory channel is oriented substantially perpendicularly to a plane encircled by the receiver coil.

6. A transmission system as defined in claim 7, wherein said acoustic convertor is a directional microphone mounted on an ear yoke engageable with patient's ear and further comprising a tension proof flexible insulating and protecting tube connected at one end thereof to said ear yoke and at the other end thereof to said fitting piece to enclose electrical conductors between said receiver and transmitter units and said acoustic convertor.

* * * * *